United States Patent
Panian (10) Patent No.: US 10,980,555 B2
(45) Date of Patent: Apr. 20, 2021

(54) METHODS AND DEVICES FOR CLOTS AND TISSUE REMOVAL

(71) Applicant: CardioProlific Inc., Reno, NV (US)

(72) Inventor: Justin P Panian, San Francisco, CA (US)

(73) Assignee: CARDIOPROLIFIC INC., Reno, NV (US)

(*) Notice: Subject to any disclaimer, the term of this patent is extended or adjusted under 35 U.S.C. 154(b) by 116 days.

(21) Appl. No.: 15/411,992

(22) Filed: Jan. 21, 2017

(65) Prior Publication Data

US 2018/0014840 A1 Jan. 18, 2018

Related U.S. Application Data

(60) Provisional application No. 62/493,679, filed on Jul. 12, 2016, provisional application No. 62/497,088, filed on Nov. 8, 2016.

(51) Int. Cl.
*A61B 17/221* (2006.01)
*A61M 1/00* (2006.01)
*A61B 17/3207* (2006.01)
*A61B 17/22* (2006.01)

(52) U.S. Cl.
CPC .... *A61B 17/221* (2013.01); *A61B 17/320725* (2013.01); *A61B 17/320758* (2013.01); *A61M 1/008* (2013.01); *A61M 1/0037* (2013.01); *A61M 1/0068* (2014.02); *A61B 2017/22034* (2013.01); *A61B 2017/320766* (2013.01); *A61B 2217/005* (2013.01)

(58) Field of Classification Search
CPC ...... A61B 17/32037; A61B 17/320725; A61B 17/320758; A61B 17/32075; A61B 17/320783; A61B 10/0283; A61B 2218/007; A61B 17/3207–2017/320791; A61B 17/3203–32037; A61B 17/320016–2017/320048; A61M 1/0003; A61M 1/0011; A61M 1/0023; A61M 1/10; A61M 1/0037; A61M 1/008; A61M 1/0068; A61M 1/0066–0076; F04B 43/02; F04B 43/04; F04B 42/02
USPC ....................................... 417/413.1; 606/127
See application file for complete search history.

(56) References Cited

U.S. PATENT DOCUMENTS

| | | | |
|---|---|---|---|
| 4,381,179 A * | 4/1983 | Pareja | F01B 19/02 29/888.02 |
| 5,792,157 A | 8/1998 | Mische | |
| 6,458,139 B1 | 10/2002 | Palmer | |
| 2002/0094285 A1 * | 7/2002 | Paolini | F04B 43/023 417/413.1 |
| 2005/0124985 A1 * | 6/2005 | Takayama | A61B 17/32037 606/15 |

(Continued)

FOREIGN PATENT DOCUMENTS

| WO | 200209599 A2 | 2/2002 |
|---|---|---|
| WO | 2014106847 A1 | 7/2014 |
| WO | 2015190575 A1 | 12/2015 |

*Primary Examiner* — Darwin P Erezo
*Assistant Examiner* — Brigid K Byrd (57) ABSTRACT

The present invention provides devices and methods for removal clots and other obstructive tissue and materials from humans located inside or outside of the patient's endovascular system using aspiration alone, and in combination with rotational maceration and aspiration.

13 Claims, 6 Drawing Sheets

(56) References Cited

U.S. PATENT DOCUMENTS

| | | | |
|---|---|---|---|
| 2009/0281485 A1* | 11/2009 | Baker | A61M 1/0058 604/35 |
| 2010/0217276 A1* | 8/2010 | Garrison | A61M 25/0662 606/128 |
| 2016/0166266 A1* | 6/2016 | Nita | A61B 17/22 606/127 |
| 2017/0238960 A1 | 8/2017 | Hatta | |

* cited by examiner

METHODS AND DEVICES FOR CLOTS AND TISSUE REMOVAL

RELATED CASES

This application relates to U.S. Provisional Application No. 62/497,088 filed on Nov. 11, 2016, entitled "Methods and Devices for Clots and Tissue Removal" and U.S. Provisional Application No. 63/493,679, filed on Jul. 12, 2016, entitled "Methods and Devices for Clots and Tissue Removal", whose entire disclosures are herein incorporated by this reference as though set forth fully herein.

BACKGROUND OF THE INVENTION

1. Field of the Invention

The present invention relates to methods and devices for removing clots, thromboembolic materials and other tissue from the human body.

2. Description of the Prior Art

In recent years, a variety of catheter devices have been developed for removal of blood clots and other tissue from the human body. There are many approaches and techniques for removing thromboembolic material from the body using either surgical or catheter based devices. These techniques are related to rotating baskets or impellers, cutters, high pressure fluid injections, Archimedes screw, vacuum, grabbing devices, rotating wires and other means as described in U.S. Pat. Nos. 4,737,153; 4,771,774; 4,923,462; 4,966,604; 5,047,040; 5,180,376; 5,226,909; 5,376,100; 5,462,529; 5,485,042; 5,569,275; 5,630,806; 695,507; 5,843,031; 5,873,882; 5,876,414; 5,911.734; 5,947,940; 5,972,019; 7,037,316; 7,179,269; 7,235,088; 7,666,161; 7,763,010; 7,842,006; 7,842,055; 7,938,820; 7,942,852; 8,062,317; 8,414,543; 8,414,543; 8,535,290, 8,545,447 and 9,463,035. Devices to fragment the clot using rotating baskets as described in U.S. Pat. Nos. 5,766,191 and 5,569,275; using cutters as described in U.S. Pat. No. 5,501,694 and using a high-pressure fluid infusion to create a Venturi effect as described in U.S. Pat. No. 5,795,322. Other devices rely on the principles of the Archimedes type screw, such as a one-piece solid machined screw to break up and/or remove clot. The U.S. Pat. No. 5,556,408 describes an atherectomy cutter employing a vacuum source for removal of loose stenotic material and other debris from a vessel. Removal of thrombus by a rotating wire is described in the U.S. Pat. No. 5,695,507. Fragmentation and removal of tissue using high pressure liquid is described in the U.S. Pat. No. 5,795,322. Atherectomy catheters with rotating elements are described in the U.S. Pat. Nos. 4,732,154; 4,886,490; 4,883,458; 4,979,939; 5,041,082; 5,135,531; 5,334,211; 5,443,443; and 5,653,696.

Other devices employ therapeutic applications of high-frequency ultrasound to achieve thrombus removal as follows: (i) ultrasound energy can be applied to break fibrin bonds and thus accelerate thrombolysis or (ii) ultrasound energy can be used directly as a tool for thrombus destruction. Also. Excimer lasers can be employed for clinical removal and debulking of thrombotic occlusions by delivering targeted laser energy to the thrombotic site, which transforms clots into a gaseous state through photochemical molecular bond breakage. Laser procedures produce minimal heat and damage to surrounding tissues. Pharmaco-mechanical thrombolysis-thrombectomy leverages the benefits of a hybrid catheter device capable of uniquely isolating the thrombolytic agent between two balloons inflated proximal and distal to the thrombotic lesion, enhancing mechanical agitation of the clot and thrombolytic agent. This procedure is often followed by aspiration of the thrombosed material to reduce systemic distribution of the thrombotic agent and thus achieve rapid revascularization without the risks of prolonged systemic thrombolytic exposure.

Catheters and techniques for blood clot removal have been well known and are successful in removing fresh and soft clots. However, there is still a need for devices and techniques that can remove well organized and variable clot sizes from endovascular and outside of the endovascular locations where clinical and technical, less invasive options are limited.

SUMMARY OF THE DISCLOSURE

The devices and methods of the present invention are applicable for removal of thromboembolic material from the human endovascular system and outside endovascular locations, as well as the removal of cancerous tissue, tumor or other particular target sites within the human body.

The clot removal devices of the present invention typically comprise an aspiration catheter, a rotational device including a rotating tubular member, shaft or wire, and an expandable braid (attached to the distal end of the rotating tubular member, shaft or wire) that is delivered through the aspiration catheter to the treatment location, and an aspiration pump with clot collecting accessories.

In one embodiment of the present invention, a clot removal device comprises an aspiration catheter having at least one axial lumen, and a rotational device. The rotational device has a rotating shaft having a distal end, and an expandable braid attached to the distal end of the shaft and extending through the lumen of the aspiration catheter. The expandable braid is delivered to a treatment site where blood clots are located from a first delivery position to a second clot engagement position, wherein in the first delivery position the expandable braid is in an unexpanded state inside the aspiration catheter having a first diameter, and wherein in the second position, the expandable braid is in a partially expanded position, having a second diameter that is greater than the first diameter when deployed outside the aspiration catheter and into clots. The braid expands outwardly during rotations and macerates surrounding clots as the braid expands to its expanded state. The braid rotates concentrically or eccentrically along its longitudinal axis and expands radially as the braid rotates. Aspiration is usually activated before the expandable braid is deployed into the clots to prevent the release of clot debris in a distal direction.

In another embodiment, the rotating shaft/wire is attached to the distal end of the expandable braid, and the proximal expandable braid section is freely movable over the rotating shaft/wire so that the expandable braid may expand to its original pre-shaped configuration either when rotated or not.

In yet another embodiment, the expandable braid may be at least 1.5 times larger in diameter in its fully expanded configuration versus its unexpanded state when inside the aspiration catheter.

In another embodiment, the rotating shaft/wire may rotate clockwise, counter clockwise, or both, and can be made of a single rotating shaft/wire, a multimember rotating shaft/wire, or a combination thereof.

In various embodiments, the device for removal of obstructive material having a rotational member can operate in rotational continuous mode, pulse mode and a combination of both. In some other embodiments, rotations of the rotational tubular member, shaft or wire can be modulated. Modulation of rotations may include speed modulation through electronic adjustment of voltage, current, as well as, pulse parameters (ON/OFF time) or any combination of all.

In yet another primary embodiment of the present invention, a small liquid pump is used in combination with a syringe that increases aspiration pressure and is suitable to oscillate suction of the aspirated blood clots to further improve the efficacy of clot removal.

As used herein, "obstructive matter" and "obstructive material" refer to the same subject matter.

As used herein, "rotational shaft/wire", "rotating shaft/wire" of the device for removal of clots from the patient refer to same component and may be rotating or not rotating during use. The "shaft/wire" can be considered to be either a shaft or a wire. All aspects and embodiments of the invention will be shown and described in attached drawings.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
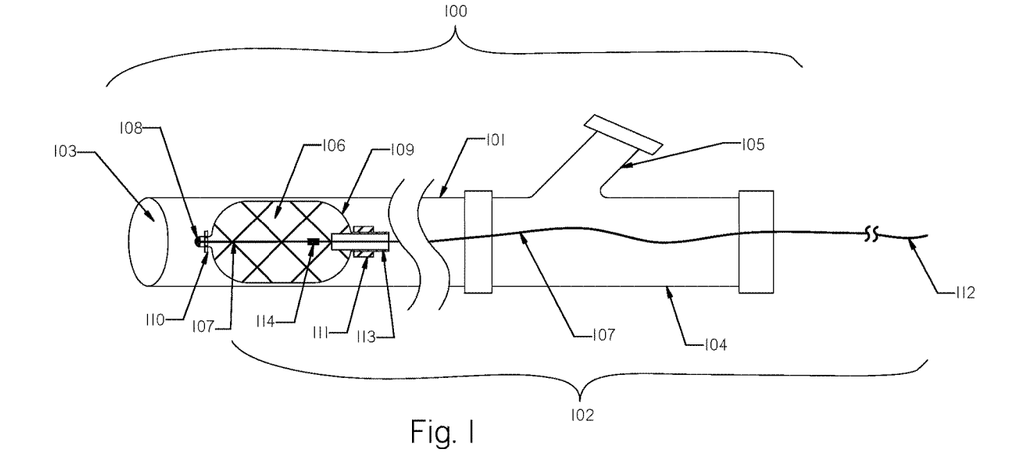
FIG. 1 is a schematic view of the clot removal device inside an aspiration catheter having a concentric expandable braid in a collapsed configuration.
Figure 2:
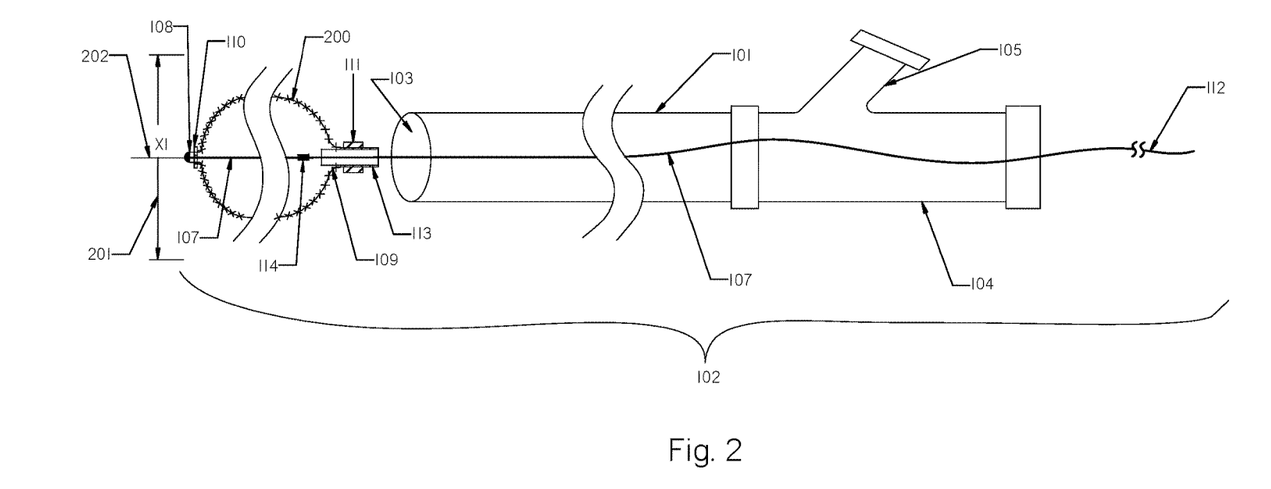
FIG. 2 is a schematic view of the clot removal device of FIG. 1 deployed outside the aspiration catheter with the expandable braid in an expanded configuration.

FIG. 1 is a schematic view of the clot removal device 100. The clot removal device 100 comprises an aspiration catheter 101 and a rotational device 102. The aspiration catheter 101 has a single axial lumen 103 and attached proximal Y-connector 104 having an aspiration port 105 to which any suitable source of suction (including handheld pumps, a stationary pump or the hospital aspiration line) may be attached. The rotational device 102 comprises an expandable braid 106 and a rotating shaft/wire 107 having a proximal end 112 attachable to a rotating source (not shown). The expandable braid 106 has a distal tip 108 that prevents the very distal end of the expandable braid 106 from distally opening or expanding when within the aspiration catheter 101 or when deployed outside the aspiration catheter 101 as shown in FIG. 2. The distal tip 108 may be made from the following materials but is not limited to: metal, polymer, rubber, adhesive or any combination thereof.

The rotating shaft/wire 107 is attached to the distal tip 108 of the expandable braid using any suitable methods, including but not limited to bonding, gluing, welding, soldering, crimping or other applicable means. The proximal end 109 of the expandable braid 108 is attached to a sleeve 113 and is freely movable along the rotational shaft/wire 107. The rotating shaft/wire 107 is freely extended inside the sleeve 113. The rotating shaft/wire 107 of the rotational device 102 may be made of metal, polymer and a combination of both, and include but is not limited to wires, rods, tubes, cables, coils, ropes and combinations thereof.

The sleeve 113 allows the attached proximal end 109 of the expandable braid 106 to experience free movement along the rotational shaft/wire 107. The expandable braid 106 may move back and forth within the aspiration catheter 101. During the delivery of the rotational device 102 to the treatment sites where clots are located (and when outside of the aspiration catheter 101), the aspiration catheter 101 travels through bends and curves related to the human access anatomy. In such situations, the rotational device 102 traverses concomitant bends as the aspiration catheter 101 when delivered through the aspiration catheter 101 to the treatment location. The expandable braid 106 may have pre-set expanded transverse shapes, including but not limited to the following configurations: circular, non-circular or a combination of both.

The rotational device 102 may have one or more radiopaque markers positioned along the expandable braid 106 for better fluoroscopic visibility. One such radiopaque marker 110 may be located on the distal tip 108 of the expandable braid 106, while another radiopaque marker 111 may be located on the proximal portion 109 of the expandable braid 106. Other radiopaque markers may be located within the expandable braid 106 or outside the expandable braid 106 along the rotating shaft/wire 107 (not shown). The radiopaque markers may also include radiopaque solder. In addition, one or more strands of the expandable braid structure may include Nitinol/Platinum composite (not shown) to improve the radiopacity of the expandable braid 106.

A stopper element 114 is positioned on the rotational shaft/wire 107 inside the expandable braid 106, and serves to prevent the expandable braid 106 from over-expansion, damage or deformations during retrieval of the expanded braid 200 (which is the same as braid 106 but given a different numeral designation to show it in its expanded state) as shown in FIG. 2 into the distal end 103 of aspiration catheter 101. The stopper 114 will allow stretching of the expandable braid 106 when moving through the aspiration catheter 101 or distally outside of the aspiration catheter 101. The stopper element may be made of metal, polymer, solder, adhesive and any other suitable material.

The rotational device 102 having a rotating shaft/wire 107 with distally attached expandable braid 106 is delivered through the lumen of the aspiration catheter 101 to the location of clots or to the treatment site. The expandable braid 106 of the rotational device 102 moves during delivery to the treatment site from the first compressed state or position as shown in FIG. 1 to a second expanded state or position as shown in FIG. 2. In the first delivery position (compressed position) the expandable braid 106 is in an unexpanded shape inside the aspiration catheter 101 and has a first diameter. In the second position, the expandable braid 106 is in an expanded position as shown in FIG. 2 and has a second diameter that is greater than the first diameter.

FIG. 2 is a schematic view of the clot removal device 100 in FIG. 1 having the expandable braid 106 of the rotational device 102 deployed outside the aspiration catheter 101 and in an expanded configuration 200. The rotational device 102 can be delivered through the lumen of the aspiration catheter 101 to the treatment location outside of the aspiration catheter 101. The expanded braid 200 may comprise between 3-48 strands formed from a plurality of Nitinol wires, having a diameter between 0.001 inches and 0.020 inches. The outside diameter X1, as shown by the bounded arrow 201 of the expanded braid 200, is between 1-40 mm. The expanded braid 200 may be formed from a plurality of strands of Nitinol wire having multiple wire strands of the same dimensions or different wire dimensions braided into the tubular shape using circular wire, oval wire, flat wire or any other suitable wire configuration or a combination thereof.

The expandable braid 106 will have radial forces exerted by the braid structure close to zero when the braid 106 is expanded to the braid 200 shown in FIG. 2. The expanded braid 200 may have some undulations, either created during manufacturing processes or induced into the braid 200, such as dents, bends, fluttering, flapping or other (not shown). The expanded braid 200 may also have a tapered section on the distal end, the proximal end, or both (not shown) to facilitate placement within blood clots. The expanded braid 200 may also comprise a continuous braid having two different dimensions or two expandable braids connected together (not shown). Such undulations of the expanded braid 200 may function to improve clinical efficiency, as described in the present disclosure.

The rotating shaft/wire 107 may rotate the expanded braid distally at about 10 to 100,000 RPM. The circular motion of the expanded concentric braid 200 along its longitudinal axis 202 has a circular-like path and the size of the covered space of its expanded size as shown by outside dimension X1.

The expanded braid 200 has attached thereto the longitudinal rotating shaft 107 whose proximal end 112 is connected to a rotational source (not shown). A rotational source may include manual rotations, motorized rotations and combination of both, and may be suitable for providing clockwise rotations, anti-clockwise and combination of both.

Figure 3:
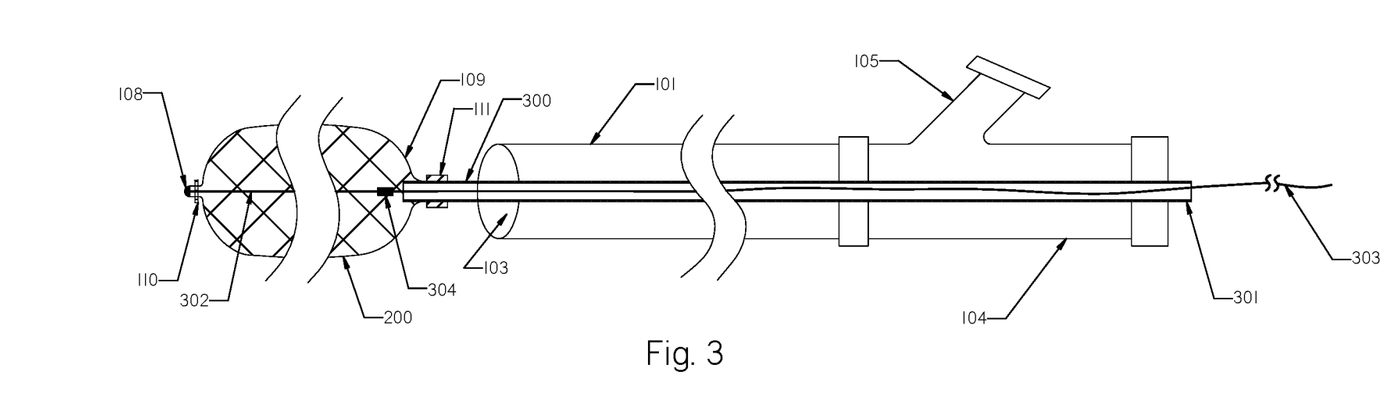
FIG. 3 shows the expandable braid having a tubular rotating member and a stopper.

FIG. 3 shows the expandable braid of FIG. 2 attached to a tubular rotating member 300. The rotating tubular member 300 is affixed to the proximal end 109 of the expanded braid 200. The proximal end 301 of the rotating tubular member 300 is connected to rotational source (not shown). When the rotating tubular member 300 spins, it also will rotate the expanded braid 200. A constraining wire 302 is freely extended within the expandable braid 200 and within the rotating tubular member 300 along its length. The distal end of the constraining wire 302 is attached to the distal tip 108 of the expanded braid 200. The proximal end 303 of the constraining wire 302 is located outside of the proximal end 301 of the rotating tubular member 300. The constraining wire 302 may be made of a polymer, metal, metal alloy or any suitable combination of all.

The expanded braid 200 may be expanded and contracted by either pulling or pushing the proximal end 303 of the constraining wire 302. The expanded braid 200 may be pushed through the lumen 103 of the aspiration catheter 101 using the rotating tubular member 300.

The stopper 304 is positioned on the constraining wire 302 inside the braid 200. The stopper 304 will allow stretching of the braid 200 when moving through the aspiration catheter 101 or distally outside of the aspiration catheter 101, and prevent the over-expansion of the braid 200 when the braid 200 is retrieved inside the inner lumen 103 of the aspiration catheter 101. The braid 200 and the attached rotating tubular member 300 move freely over the constraining wire 302, and the constraining wire 302 moves freely inside the rotating tubular member 300.

The rotating tubular member 300 is made of a tube while the rotating shaft/wire 107 shown in FIG. 1 can be made of wire. Several other shaft configurations may be used to rotate the expandable braids of the present invention, including but not limited to multiple wires, rod, tubes, cable, coil or combinations thereof. Such rotating shafts may be made of metal, metal alloys, polymers or combination of all.

The constraining wire 302 is attached to the distal tip 108 of the braid 200 and extended proximally within the rotating tubular member 300, and may be pulled and pushed within the rotating tubular member 300 to control expansion of the braid 200 (not shown) using its proximal end 303. Pushing the constraining wire 302 distally with respect to rotating tubular member 300 will stretch the braid 200, while pulling the proximal end 303 of the constraining wire 302 proximally with respect to the rotating tubular member 300 will enlarge the braid 200.

Figure 4:
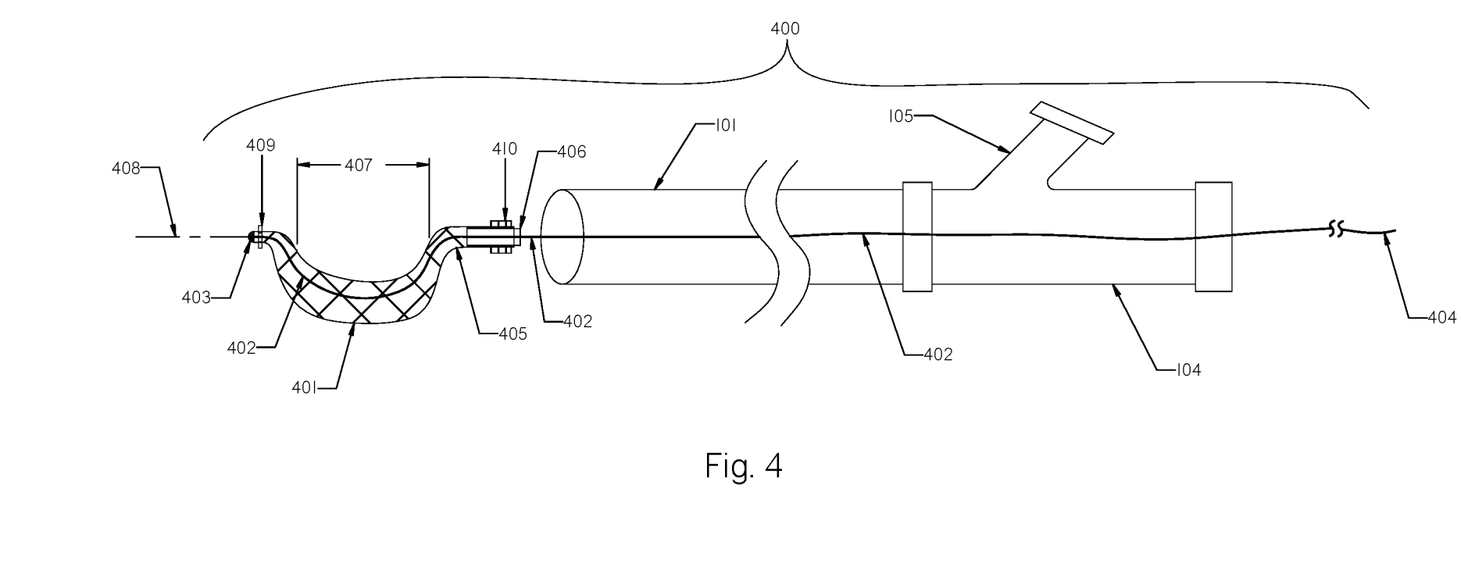
FIG. 4 is a schematic view of an alternative clot removal device having an eccentric expandable braid configuration deployed outside the aspiration catheter.

FIG. 4 is a schematic view of an alternative clot removal device 400 having an eccentric expandable braid 401 that is deployed outside the aspiration catheter 101. The rotating shaft 402 is connected to a distal end 403 of the expandable braid 401 and is connected to a rotation source at its proximal end 404. The proximal end 405 of the expandable braid 401 is attached to a sleeve 406 and may freely move longitudinally along the rotating shaft 402. The distal portion of the rotating shaft 402 located inside the expandable braid 401 undergoes a bend that is shaped to produce the eccentricity of the expandable braid 401. The expandable braid 401 is attached to the rotational shaft 402 in an off-centered manner to provide an off-centered angular motion of the expandable braid 401. When the off-centered braid 401 rotates, it follows a circular path that is significantly larger in size compared to a center-rotating braid, thereby enabling more efficient separation of thromboembolic material from a larger area that it covers while rotating.

Several methods may be employed to form an eccentric braid configuration. The eccentric expandable braid example as shown in FIG. 4 is a simple deflection of the middle braid portion 407 out of the longitudinal axis 408. Since the expandable braid 401 is made of Nitinol wires, the most common and practical approach to forming such eccentricity or deflection would be through heat forming. Heat forming of the expandable braid 401 provides many different options and choices to configure the eccentricity of the expandable braid 401 as desired to best serve its desired clinical functions.

The expandable braid 401 shown in FIG. 4 has a tubular configuration with circular or non-circular cross-section and has the majority of its middle part 407 pre-shaped eccentrically with reference to longitudinal axis 408. The expandable braid 401 has one radiopaque marker 409 located on the distal end 403 and another radiopaque marker 410 located on the proximal end 405 of the expandable braid 401.

The present invention provides options and possibilities for shaping the braid 401 in any desirable eccentric configuration suitable to be used as a rotational distal member. While FIG. 4 shows a specific eccentric expandable braid configuration 401, pre-shaping of the expandable braid 401 described in the present invention is not limited to this specific configuration. For example, one or more of the modifications for the eccentric braid 401 may be made to accommodate a different anatomical configuration where the clot removal device 400 may be used.

Figure 5:
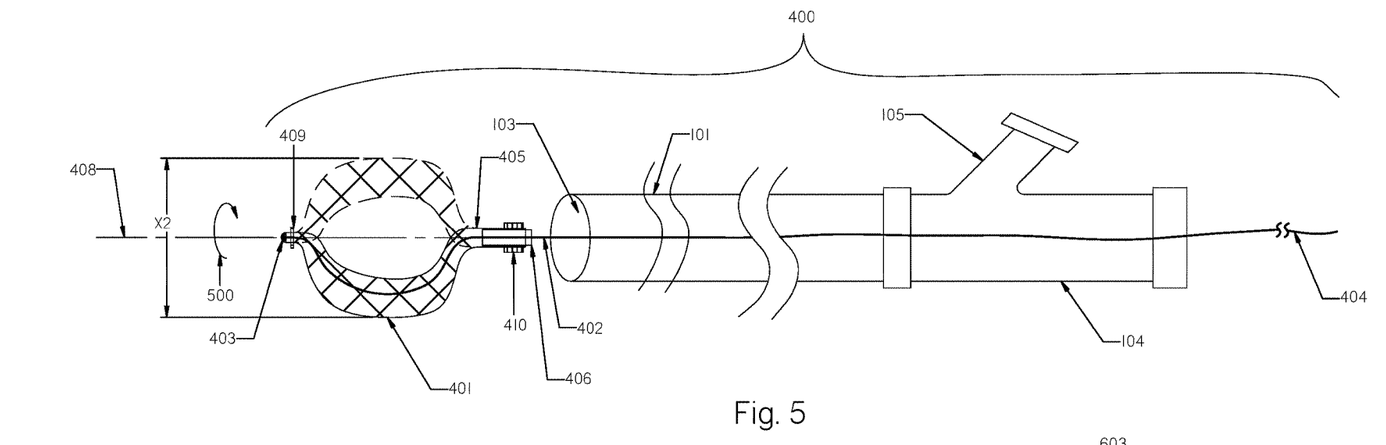
FIG. 5 shows the clot removal device of FIG. 4 with the eccentric expandable braid rotating.

FIG. 5 shows the clot removal device 400 of FIG. 4 with the eccentric expandable braid 401 rotating clockwise along the longitudinal axis 408 as shown by arrow 500. It is important that the distal end 403 and the proximal end 405 of the expandable braid 401 rotate adjacent to or near the same longitudinal axis 408 to provide stability during rotation and to avoid potential trauma to surrounding tissue while the eccentric expandable braid 401 is encircling eccentrically within the treatment area. When the expandable braid 401 rotates as shown by arrow 500, it covers radial space outlined by the diameter X2, which is a significantly larger space than the space covered by the concentric expanded braid 200 shown in FIG. 2. This feature of the rotational eccentric expandable braid 401 provides a much larger covered space compared to the concentric rotational braid 200 shown in FIG. 2, and the advantage of such expansion is demonstrated in FIG. 8.

Figure 6:
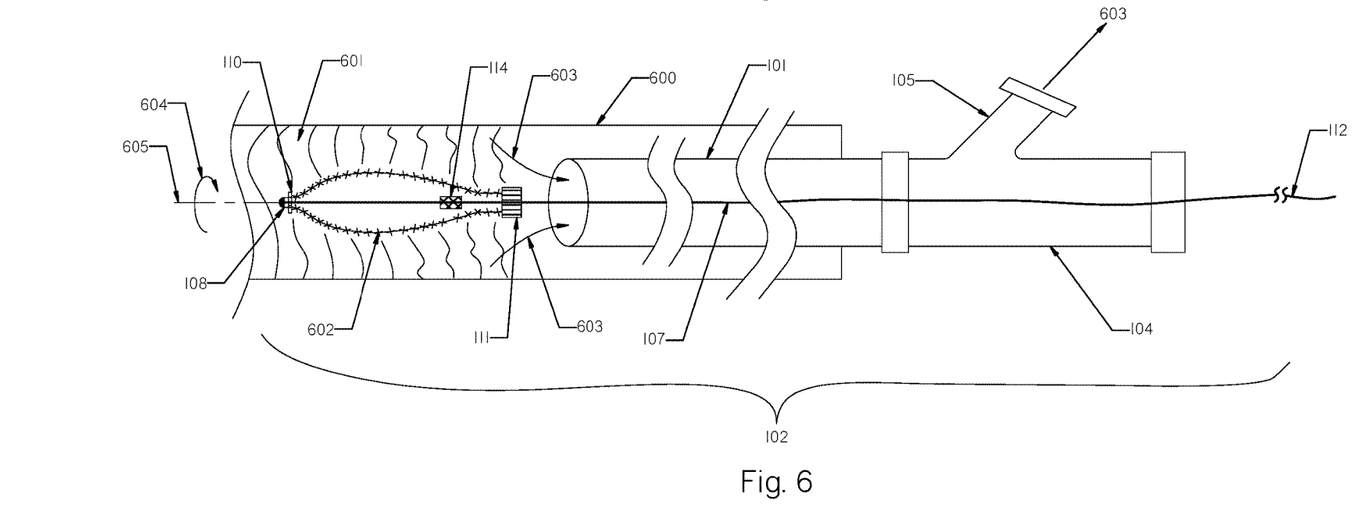
FIG. 6 illustrates the clot removal device of FIGS. 1 and 2 with the concentric expandable braid placed within clots to be removed.

FIG. 6 shows the clot removal device of FIG. 2 placed inside clots 601 within the blood vessel 600. The placement of the aspiration catheter 101 within the blood vessel 600 and proximally to clots 601 is accomplished through the use of any suitable guide wire and is well known in the art. After positioning the aspiration catheter 101 at clots 601, the clot removal device 100 is introduced through the aspiration catheter 101 as shown in FIG. 1 into the clots 601. The expandable braid 106 as shown in FIG. 1 assumes a partially expanded position 602 when deployed inside the clots 601. To minimize the release of any clot particles during the deployment of the expandable braid 106 outside the aspiration catheter 101 and into clots 601, suction at the proximal port 105 is activated and the distal end of the aspiration catheter 101 begins to aspirate clots 601 as shown by arrow 603. Aspiration remains active until all clots 601 are removed.

Figure 7:
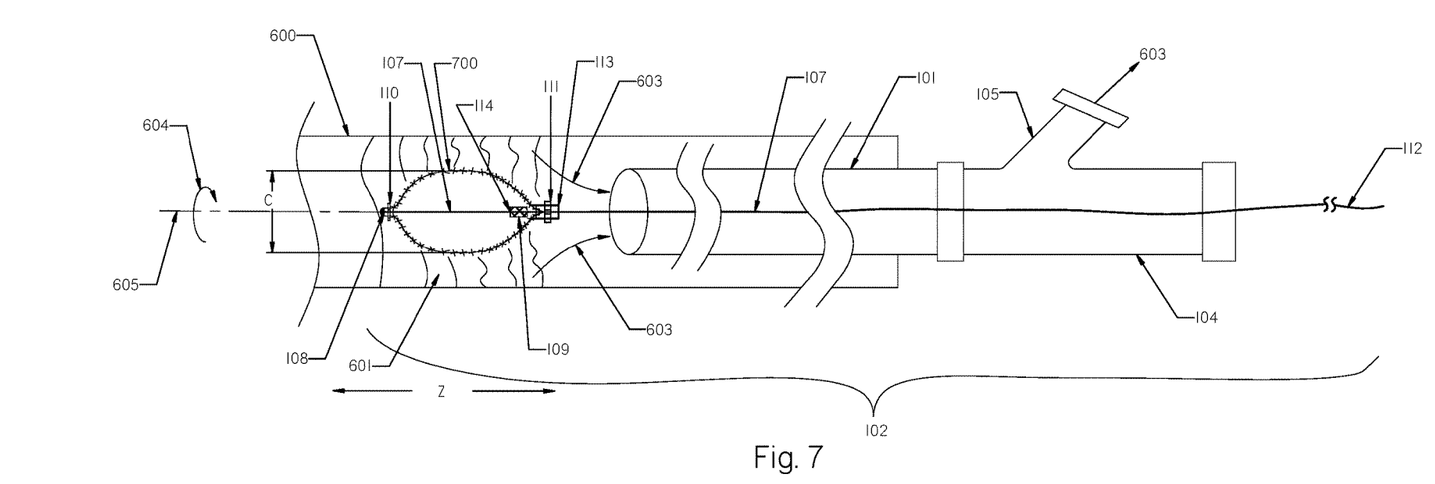
FIG. 7 shows the clot removal device of FIGS. 1 and 2 inside clots with the concentric expandable braid fully expanded.

After placement of the partially expanded braid 602 within clots, the braid 602 begins to rotate as shown by arrow 604. While the braid 602 rotates, crossing wires of the braid structure interlace the clots 601 and start acting like helical blades, thereby cutting, trimming, notching, slashing and lacerating the surrounding clots 601. Such clot maceration process by rotating the expandable braid 602 continues and lasts as long as the expandable braid 602 interfaces or is in contact with clots 601, and until the rotating braid 602 reaches a fully expanded position 700 as shown in FIG. 7. The expanded braid 700 shown in FIG. 7 is the same as the expanded braid 200 shown in FIG. 2, even though they may appear different because the braid 700 is inside a clot 601 while the braid 200 is unconstrained.

The expandable braid 602 engaged in clots 601 may also at least partially rotate clots 601 within the vessel 600 (not shown). Such rotation of clots 601 within the vessel 600 may further facilitate blood clot removal and prevent the aspiration catheter 101 from clogging.

A continuous suction during the maceration of the clots 601 will remove clots outside of the treatment area. Using the concentric rotating braid 602, clots will be removed from the space equal to the expanded braid tubular dimension as shown in FIG. 7 where the braid 602 reaches its expanded shape 700. The circular motion of the braid 602 along its longitudinal axis 605 has a circular-like path and the size of the covered cylindrical space while the braid 602 is rotating equals the expanded braid size.

A method for removing clots from a blood vessel comprises the steps of providing a clot removal device 100 as shown in FIG. 1 incorporating an aspiration catheter 101 having at least one lumen 103 and a rotational device 102 having a rotating shaft 107 with a distally attached expandable braid 106 that is deliverable through the lumen 103 of the aspiration catheter 101, placing the distal end of the aspiration catheter 101 proximally to the clots 601 in the vessel 600 as shown in FIG. 6, advancing the rotational device 102 through the aspiration catheter 101, deploying the braid 602 outside of the distal end of the aspiration catheter 101 and inside the clots 601 as shown in FIG. 6, activating aspiration at the aspiration port 105 as shown by arrow 603 to begin suction of the clots outside the blood vessel 600, and rotating the rotational device 102 as shown by arrow 604 to macerate the clots 601. The braid 602 rotates co-axially along its longitudinal axis 605 as shown in FIG. 6 and expands radially to become the radially expanded braid 700 shown in FIG. 7. After the procedure is completed, the clot removal device 100 is removed.

FIG. 7 shows the clot removal device of FIG. 6 with the expandable braid 700 that reaches a fully expanded position. The proximal end 109 of the concentric expandable braid 700 is freely movable along the rotational shaft 107. The expandable braid 106 as shown in FIG. 1 within the aspiration catheter 101 will expand into a partially expandable position 601 after deployment from the aspiration catheter 101 as shown in FIG. 6 and continue to expand when rotating and macerating clots 602 to its original pre-shaped configuration 700 as shown in FIG. 7.

When the expandable braid 106 is released into blood clots, it assumes a partially expandable position 602 because the outward braid forces are not able to allow a full braid release and create expansion resistance within clots 601. However, when the expandable braid 602 starts to rotate and macerate clots 601, the expandable braid 700 reaches its fully expanded position while macerated clots are aspirated outside the aspiration port 105.

The braid 602 is radially expanding from the first placement position inside clots 601 as shown in FIG. 6 to a second rotational position, which is the expanded braid 700 as shown in FIG. 7. In the first placement position as shown in FIG. 6, the braid 602 is in a partially expanded state inside the clots 601 and has a first diameter. In the second rotational position, the braid 700 is in a radially expanded position, having a second diameter greater than the first diameter when positioned within the clots as shown in FIG. 7.

The fully expanded braid 700 rotating co-axially along it longitudinal axis 605 covers a cylindrical space having diameter C. Also, to macerate more clots 601, the rotating expanded braid 700 may be moved back and forth within the clots 601 as shown by the distance Z, thereby macerating clots along a length along its cylindrical space within the vessel 600 (not shown).

The partially expanded braid 602, after introduction into the clots 601 (FIG. 6), may also be utilized to ablate clots without rotations. The braid 602 attached to the shaft 107 as shown in FIG. 1 and the braid 200 attached to the rotating tubular member 300 (FIG. 3) may be moved longitudinally back and forth as shown by the arrow Z within the clots 601 (see FIG. 7) and without rotations. Such movement of the braid 602 within clots 601 will cut, separate, and macerate clots, and provide an alternative option to facilitate clot removal. The eccentric braid 400 (FIG. 3) may also be moved back and forth after introduction in to clots without rotations to macerate the clots.

Figure 8:
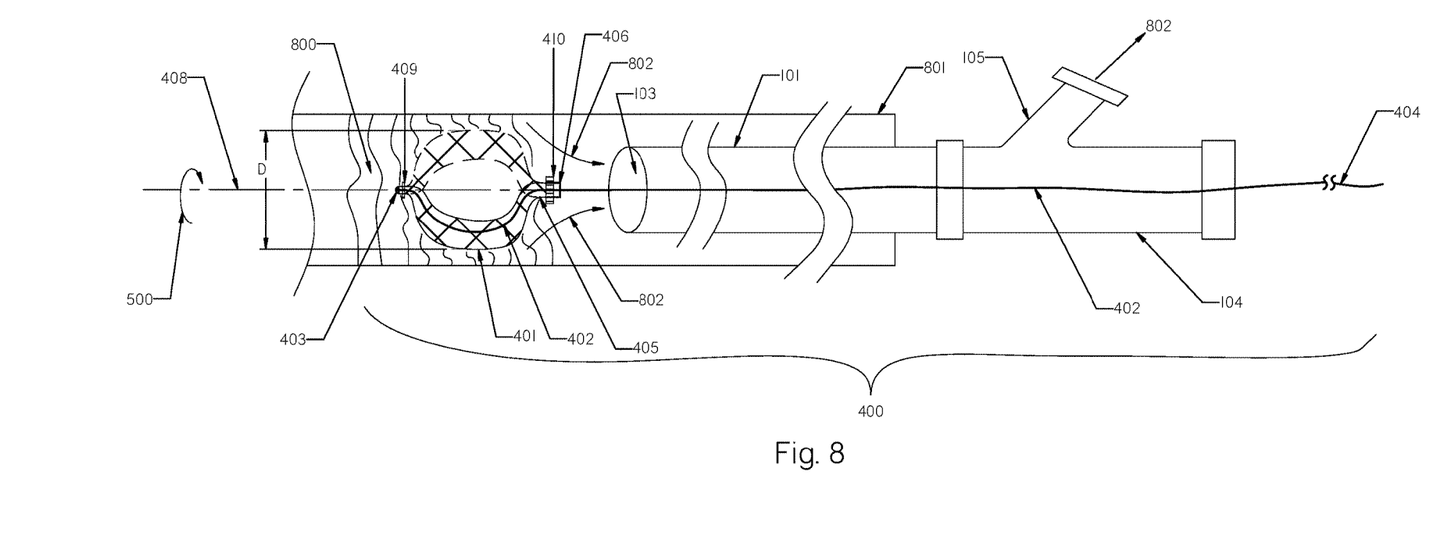
FIG. 8 shows the clot removal device of FIG. 3 inside clots to be removed having an eccentric expandable braid rotating when fully expanded.

FIG. 8 shows the clot removal device 400 of FIG. 4 with the eccentric expandable braid 401 placed within clots 800 inside the vessel 801. Placement of the clot removal device 400 inside clots 801 is similar to the method described in connection with FIG. 6, and includes providing a clot removal device 400 comprising an aspiration catheter 101 having at least one lumen 103 and a rotational device 400 having a rotating shaft 402 with a distally attached braid 401 that is deliverable through the lumen 103 of the aspiration catheter 101, placing the distal end of the aspiration catheter 101 proximally to the clot location 800 in the vessel 801, advancing the rotational device (the braid 401 with attached rotational shaft 402 having the distal portion 406 located inside the braid 401 and proximal portion 404 attached to a rotational source) through the aspiration catheter 101, deploying the braid 401 outside of the distal end of the aspiration catheter 101 and inside the clots 800, activating aspiration as shown by arrow 802 to begin suction of the clots through the port 105 of the aspiration catheter 101 outside the blood vessel 801, and rotating the eccentric braid 401 to macerate clots 801. The eccentric braid 401 rotates eccentrically along its longitudinal axis 408 and expands radially creating a cylindrical space D within clots 800.

Such eccentric braid 401 configuration or braid having undulation/deformation will cause the braid 401 to undergo angular rotation around the longitudinal axis 408 covering the cylindrical space having the diameter D. Forces applied at a distance away from an axis 408 of rotation called eccentric forces will cause a rotational moment (torque) that may cut, macerate, and ablate blood clots and other tissue.

When the eccentric braid 401 rotates (as shown by arrow 500) away from the axis 408 of rotation, it will also undergo transverse motions or displacement (not shown). Likewise, vibrations may be created using eccentric rotating masses through the release of pressure waves while rotating the eccentric braid 401 along the axis 408. Both these actions may further contribute to maceration or homogenization of blood clots (not shown).

In practical use, torque, transverse forces and vibrational energy will be applied to the clots to be removed while the eccentric braid 401 rotates inside clots 800 within the vessel 801 to further break, agitate, smash or liquefy the clots 800. Aspiration activation at the port 105 is needed from the beginning of the introduction of the expandable eccentric braid 401 into clots until clot removal is completed to secure the efficient removal of clots, and to prevent any clot debris from travelling distally.

When the aspiration catheter 101 becomes clogged because the aspiration forces are unable to suck the clot through the inner lumen 103 of the aspiration catheter 101, the braids of the present invention may be at least partially pulled back into the inner lumen 103 of the aspiration catheter 101 to unclog the aspiration catheter 101 by forcing the clogging clots to move proximally and to be aspirated through the port 105 of the aspiration catheter 101 outside the patient (not shown in the figures). The braid that is retrieved inside the aspiration catheter 101 exerts pressure against the thromboembolic material in a radially inward direction to facilitate removal of thromboembolic material and unclogging, as well as preventing the aspiration catheter from experiencing more clogging.

The braids of the present invention exert radial forces within the clots and expand during rotations inside the clots to a cylindrical configuration that is usually smaller than the size of the vessel to avoid injury to the vessel. The braids and other rotational members of the present invention may rotate within the range from 10 RPM to about 100,000 RPM and may rotate in one of the following modes: clockwise, counterclockwise or a combination of both, and such rotations may be manual, motorized or a combination of both.

The braids of the present invention may be repositioned inside the vessel back and forth after deployment into clots and/or during rotations. Such repositioning may be used for a better and more complete clot removal from the treatment area. The braids of the present invention are configured to assume a radial configuration and the braids exert radial forces against the clot edifice when deployed from the aspiration catheter and into clots.

The aspiration catheter of the present invention should have a sufficient flexibility to navigate the vasculature of the patient or any other access area to clots or tissue to be removed. The aspiration catheter should have an inner lumen diameter sufficient to permit delivery and retraction of the braid into the lumen of the aspiration catheter when the braid is partially or fully deployed outside the distal end of the aspiration catheter.

The clot removal devices of the present invention may include means to apply a maximum aspiration pressure/ maximum suction within the aspiration catheter instantaneously. Such means may include aspiration switches or Touhy-Borst valves that are well known in the art to build up suction pressure to a maximum when the valve is turned off and then suddenly turn on the valve to apply it to clots to be removed.

The braids of the present invention may include means within its structure to improve maceration and cutting capability, including but not limited to: use of a different wire dimension for the braid; use of a different wire shape within the braid structure that may include but is not limited to a circular wire, non-circular wires, flat wire and combinations thereof; and use of dents and deformations within the expandable braid structure.

Figure 9:
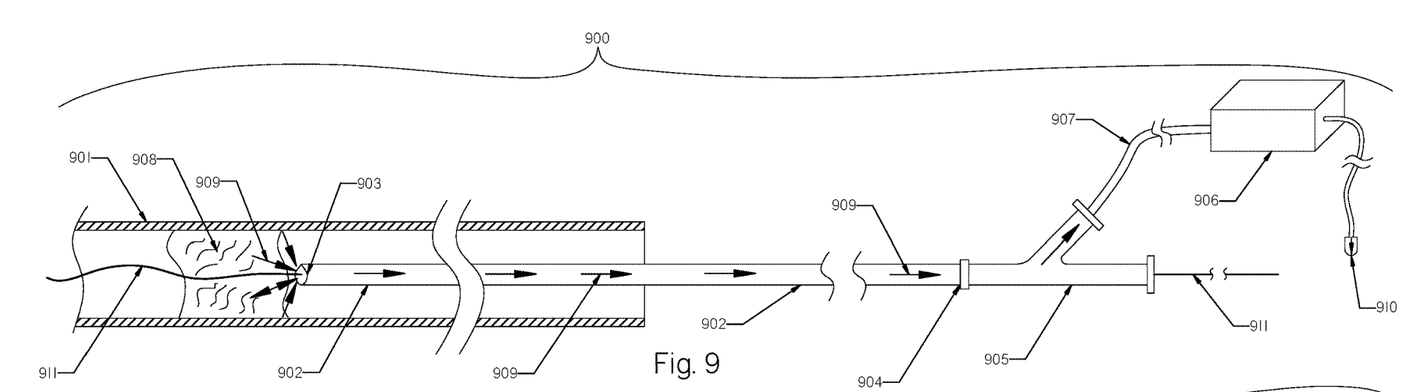
FIG. 9 shows a blood clot removal device partially located inside the vessel with an aspiration catheter attached to a disposable hand-held aspiration pump.

FIG. 9 shows a blood clot removal device/system 900 which is partially located inside the vessel 901. The clot removal system 900 comprises an aspiration catheter 902 having a distal end 903 and proximal end 904 with an attached Y-connector 905. The aspiration catheter 902 can be the same as the aspiration catheter 101. A hand-held aspiration pump 906 is attached to the side arm of the Y-connector 905 via a tube 907. The distal end 903 of the aspiration catheter 902 is positioned adjacent to blood clots 908 to be removed and located within the vessel 901. Activation of the pump 906 will instantaneously create a maximum vacuum pressure within the aspiration catheter 901 and at the distal end 903 of the aspiration catheter 902. Such maximum pressure is usually produced within 1-15 seconds, and preferably for less than 10 seconds. Arrows 909 show the direction of aspiration into the distal end 903 of the aspiration catheter 902 and along the inner lumen of the aspiration catheter 902 toward the pump 906 and clot bag 910. While under vacuum from the pump 906, blood clots 908 will begin to move inside the distal end 903 of the aspiration catheter 902, through the aspiration catheter 902 towards the pump 906, and ultimately collected in the bag 910. Aspirated blood clots 908 will be further macerated by the pump 908 and in a liquid form collected inside the bag 910. The system 900 is a single use device that is disposed of after the procedure. Preferably, the blood clot removal device/system 900 is sterilized by known methods including Ethylene Oxide (ETO), E-Beam or Gamma Irradiation, so it can be operated by a physician within a patient adjoining a sterilized field.

Alternatively, a guide wire 911 may be positioned within the aspiration catheter 902 for placement or navigation within the vessel 901.

Most of aspiration systems or pumps available in the medical field industry are based on air aspiration and the collection of blood clots in a rigid container. One disadvantage of such method includes a delay in building up a maximum air pressure within the blood collecting container and the entire aspiration system because air is highly compressible. Use of liquid pumps for such application may overcome such a limitation. However, such use of liquid pumps will, be limited to single-use devices due to pump contamination during use since aspirated material is flowing through the pump. Liquid pumps will apply a maximum pressure instantaneously which may significantly improve the efficacy of blood clot aspiration.

One suitable pump for use in clot aspiration are membrane pumps, also known as diaphragm liquid pumps, which use a combination of the reciprocating action of a rubber or thermoplastic diaphragm, and suitable shut-off valves on either side of the diaphragm to pump a fluid. A relatively simple design uses a circular power from the motor which converts into vertical eccentric movement transferred to a diaphragm. The diaphragm is sealed with one side in the fluid to be pumped, and the other in air or hydraulic fluid. The diaphragm is flexed causing the volume of the pump chamber to increase and decrease, and not only aspirates blood clots, but also macerates blood clots flowing through. The handheld liquid aspiration pump 906 may be used in any position, works without lubricants, and can be powered by conventional single or multiple batteries, or can be connected to power line with or without voltage convertors.

The highest possible aspiration pressure that such single use disposable pumps can produce will provide a better efficacy in removing clots. There are two main attributes of aspiration pressure of a diaphragm pump that can be maximized: the diaphragm moves (stroke) and the speed of a motor at which the diaphragm reciprocates within the pump. The recommended speed of the motor should be more than 2,000 RPM to about 10,000 RPM, preferably around 5,000 RPM. The diaphragm stroke should be more than to about 0.010" and less than 0100", preferably 0.040".

Diaphragm pumps are sensitive to particles because of check valves in the suction and discharge sites of the pump head. If either valve becomes stained or contaminated, the pump will lose its prime. While such valve-contamination scenarios are expected during the removal of blood clots, a simple way to overcome such a limitation is to keep the pump working continuously without turning it ON/OFF during the blood-clot removal procedure.

Figure 10:
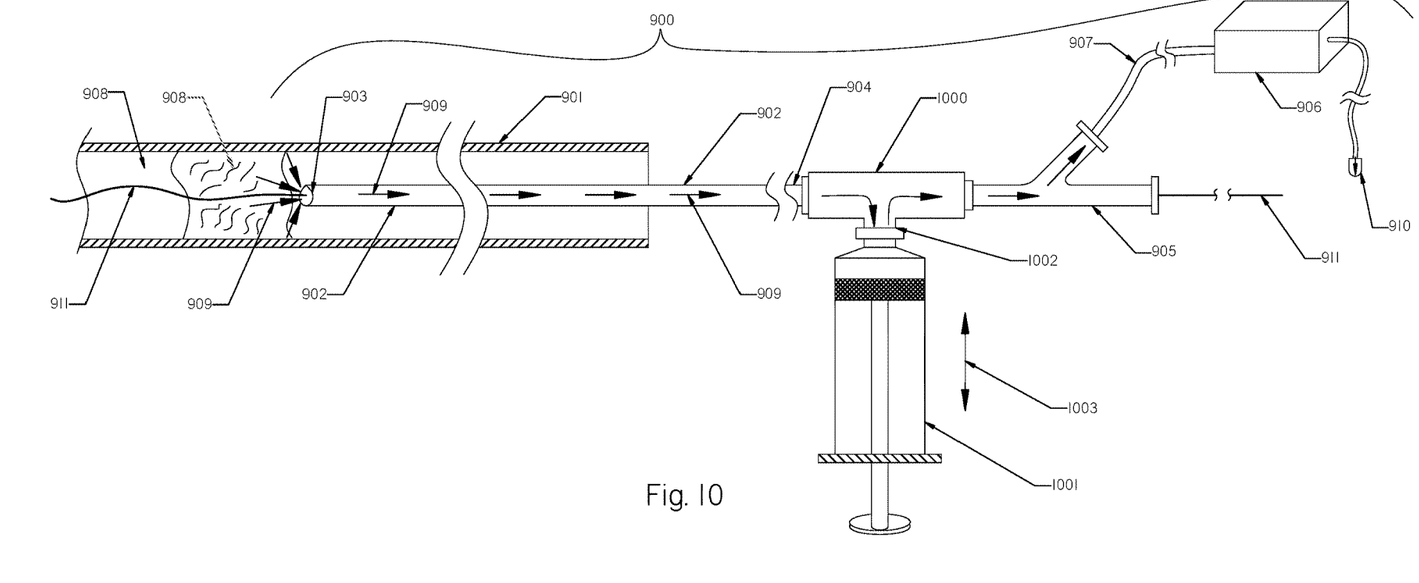
FIG. 10 shows the same blood clot removal system of FIG. 9 with the addition of a syringe.

FIG. 10 shows the same clot removal device/system as in FIG. 9 with the addition of a T-connector 1000 and a syringe 1001. The T-connector is attached to the proximal end 904 of the aspiration catheter 902 and to the Y-connector 905. The third arm of the T-connector 1002 is attached to the syringe 1001. Alternatively, the T-connector may be attached to the syringe 1001 via additional tubing (not shown)

A pair of non-return check valves is located inside the pump 906 (not shown) that prevents reverse flow of the aspirated blood clots 908. Such non-return valves will help to use syringe 1001 to further increase aspiration pressure within the aspiration catheter 902, because all additional vacuum created by the syringe 1001 will apply along the aspiration catheter 1001.

During the removal of blood clots 908 from the vessel 901 which is in a closed liquid sphere or environment, pulsation or modulation of the aspiration pressure within the aspiration catheter 902 may boost blood clot removal by further inducing more fracture and micro-cracks within the clot structure, thereby changing the compliance of the clots and enabling or facilitating removal of the clots outside the patient. A conventional method of such pulsation may include turning the motor of a liquid pump to ON/OFF duty cycling of current/voltage modulation, causing low-high liquid aspiration pressure according to methods that are well known in the art.

The syringe 1001 may also be suitable for pulsing aspiration pressure within the aspiration catheter 902 by moving the syringe plunger back and forth as shown by arrow 1003. A non-return valve within the pump 906 (not shown) will always be closed under an additional vacuum created and applied by the syringe 1001 within the aspiration catheter 902.

Figures 11, 12:
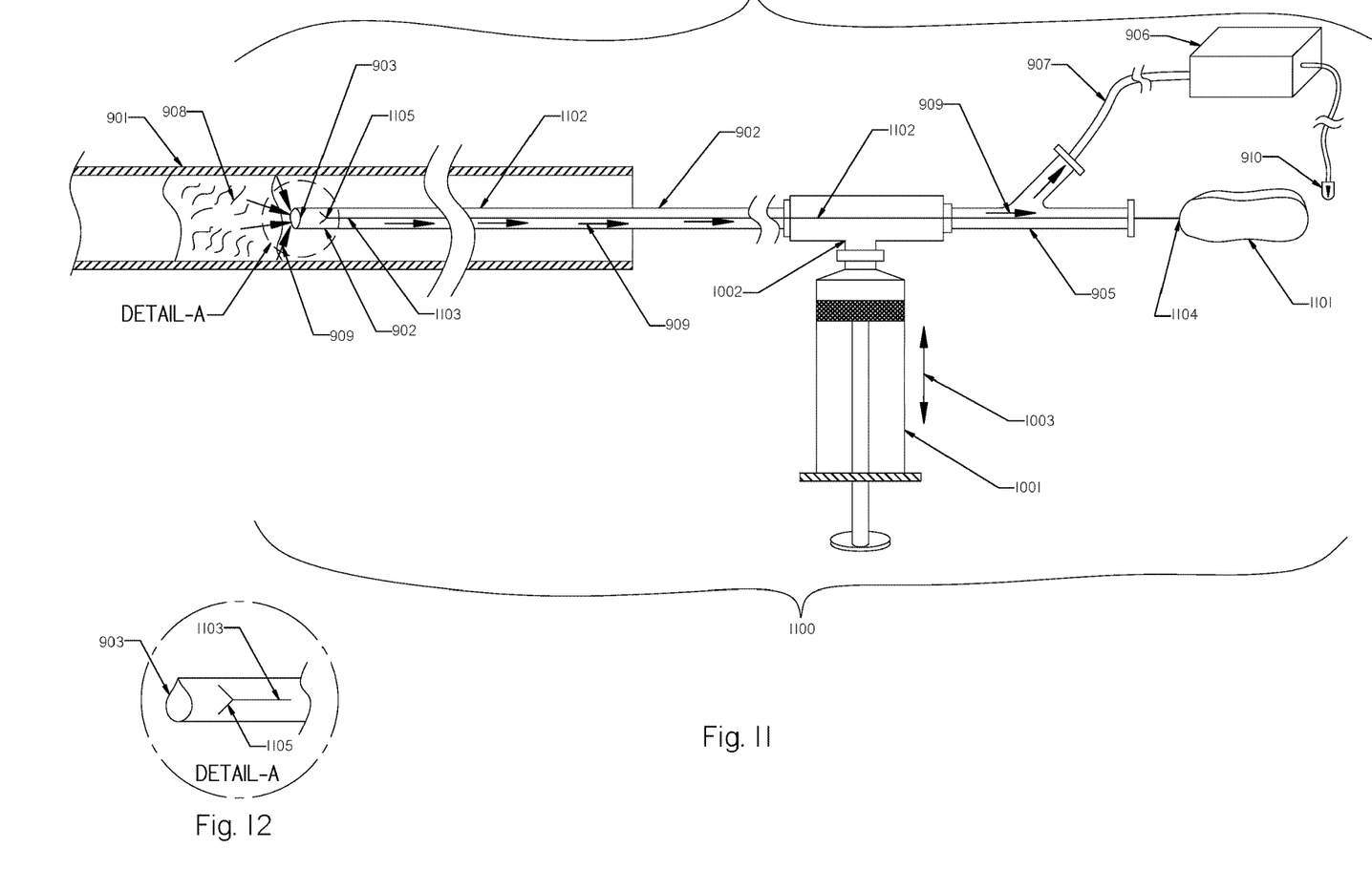
FIG. 11 shows the blood clot removal system of FIG. 10 with the addition of a rotational member.
FIG. 12 is an enlarged view of the section labeled "A" in FIG. 11.

FIG. 11 shows the blood clot removal device/system of FIG. 10 with the addition of a rotational assembly 1100. The rotational assembly 1100 comprises a motor 1101 and a rotational shaft/wire 1102 that extends at least partially within the aspiration catheter 902. The rotational shaft/wire 1102 has a distal end 1103 and a proximal end 1104. The proximal end 1104 of the rotational shaft/wire 1102 is attached to the motor 1101. The rotational shaft/wire 1102 may be made of wire, cable, tube, rod or any combination thereof. A shape or bend 1105 is located on the distal end 1103 of the rotational shaft/wire 1102 for macerating or breaking up blood clots. The distal shape 1105 may be located within the aspiration catheter 902, outside the aspiration catheter 902, or may be repositioned back and forth as required.

A variety of shapes may be provided on the distal end 1103 of the rotational shaft/wire 1102 or attached to the distal end 1103 of the rotational shaft/wire, including but not limited to, a sinusoidal shape, Y-shape, T-shape, V shape, loop and any other shapes or configuration suitable for breaking up blood clots.

The rotational shaft/wire 1102 may also be manually rotated using an operator's hand or fingers. However, the addition of the motor 1101 may be helpful when blood clots are older and well organized. Various alternative embodiments may involve use of such rotational medical devices to remove blood clots or other tissue located in other parts of a patient's body, either inside or outside of the patient's endovascular system. Locations inside the endovascular system may include, but are not limited to, the arterial system, the venous system, fistulas, vascular grafts and/or combinations thereof. Locations outside the endovascular system may include, but are not limited to, internal organs and the head. In some embodiments, one or more minor device modifications may be made to the embodiments of the systems described above, to accommodate a different anatomical usage within the body. For example, in one embodiment, the blood clot removal device may have a flexible, rather than a stiff, rotational shaft to facilitate accessing clots in a different part of the body.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A device for removing obstructing matter from human body, comprising:
   an aspiration catheter having at least one lumen, a distal end to be positioned by the obstructing matter and a proximal end, the aspiration catheter configured for aspiration from the distal end toward the proximal end;
   a T-connector attached by a first arm to the proximal end of the aspiration catheter;
   a Y-connector attached to a second arm of the T-connector;
   a liquid diaphragm pump attached via a side arm of the Y-connector to the second arm of the T-connector, the liquid diaphragm pump applying vacuum to the aspiration catheter, wherein a diaphragm reciprocates within the liquid diaphragm pump at a speed higher than 2000 RPM, wherein the diaphragm has a stroke more than 0.010", wherein the liquid diaphragm pump produces maximum pressure within less than 15 seconds from activation of the liquid diaphragm pump; and
   a syringe attached to a third arm of the T-connector, wherein additional vacuum created by the syringe is applied to the aspiration catheter to increase aspiration pressure into the distal end of the aspiration catheter.

2. The device of claim 1, further including a rotational member having a distal end and a proximal end that can be rotated and longitudinally moved back and forth within the aspiration catheter, wherein the distal end of the rotational member has a bent shape, and wherein the rotational member is at least partially positioned within the aspiration catheter.

3. A device for removing obstructing matter from human body, comprising:
   an aspiration catheter having at least one lumen, a distal end to be positioned by the obstructing matter and a proximal end, the aspiration catheter configured for aspiration from the distal end toward the proximal end;
   a T-connector attached by a first arm to the proximal end of the aspiration catheter;
   a Y-connector attached to a second arm of the T-connector;
   a liquid diaphragm pump attached via a side arm of the Y-connector to the second arm of the T-connector, wherein the liquid pump produces maximum pressure within less than 15 seconds from activation of the liquid pump: and
   a syringe attached to a third arm of the T-connector, the syringe applying vacuum to the aspiration catheter to increase aspiration pressure into the distal end of the aspiration catheter.

4. The device of claim 3, further including a rotational member having a distal end and a proximal end that can be rotated and longitudinally moved back and forth within the aspiration catheter, wherein the distal end of the rotational member has a bent shape, and wherein the rotational member is at least partially positioned within the aspiration catheter.

5. The device of claim 3, wherein the liquid pump is a membrane pump.

6. The device of claim 5, wherein the membrane pump includes a component that reciprocates at a speed between 2000 RPM and 10,000 RPM.

7. The device of claim 5, wherein the membrane pump includes a component that reciprocates at a speed between 3000 RPM and 7,500 RPM.

8. The device of claim 5, wherein the membrane pump includes a component that reciprocates at a speed between 4000 RPM and 6,000 RPM.

9. The device of claim 5, wherein the membrane pump includes a component that reciprocates at a speed of 5000 RPM.

10. The device of claim 5, wherein the membrane pump has a stroke between 0.010 inches and 0.100 inches.

11. The device of claim 5, wherein the membrane pump has a stroke between 0.020 inches and 0.080 inches.

12. The device of claim 5, wherein the membrane pump has a stroke between 0.030 inches and 0.060 inches.

13. The device of claim 5, wherein the membrane pump has a stroke of 0.040 inches.

* * * * *